United States Patent [19]
Catherall

[11] 3,955,401
[45] May 11, 1976

[54] APPARATUS FOR DETERMINING THE DENSITY OF A FLUID

[75] Inventor: Reginald Catherall, Woking Surrey, England

[73] Assignee: Bell & Howell Company, Chicago, Ill.

[22] Filed: Apr. 28, 1975

[21] Appl. No.: 571,970

Related U.S. Application Data

[63] Continuation-in-part of Ser. No. 487,386, July 11, 1974.

[30] Foreign Application Priority Data

July 16, 1973  United Kingdom............... 33743/73

[52] U.S. Cl.................................................. 73/32 A
[51] Int. Cl.²........................................... G01N 9/00
[58] Field of Search..................... 73/30, 32 A, 32 R

[56] References Cited
UNITED STATES PATENTS 2,635,462  4/1953  Poole et al........................... 73/32 A
3,444,723  5/1969  Wakefield........................... 73/32 A

*Primary Examiner*—James J. Gill
*Attorney, Agent, or Firm*—David Weiss

[57] ABSTRACT

Apparatus for determining the density of a liquid comprises a resilient tube coupled at each end through resilient couplings to support flanges for connection in a pipeline or the like. Two cantilevers of the same material and cross section as the tube are secured to the tube so that they have a common axis parallel to that of the tube and their free ends are directed towards each other. The tube and cantilever are so excited that they vibrate in antiphase at the same transverse frequency of vibration, the frequency of the vibration being dependent upon the density of liquid in the tube. The cantilevers are provided with an annular collar at their free ends such that when the tube is filled with a liquid of a predetermined density the root shear force and bending moment of each cantilever cancels those of the tube.

29 Claims, 6 Drawing Figures

APPARATUS FOR DETERMINING THE DENSITY OF A FLUID

CROSS-REFERENCE TO RELATED APPLICATION

This application is a continuation-in-part of U.S. Application Ser. No. 487,386, filed July 11, 1974.

BACKGROUND OF THE INVENTION

This invention relates to apparatus for determining the density or specific gravity of a fluid.

It is known that the frequency of vibration of a resonant body is dependent, inter alia, upon the density of a fluid in contact with the body.

DISCUSSION OF THE PRIOR ART

One such apparatus which makes use of this knowledge comprises two identical, resilient tubes arranged in spaced, parallel relation and secured together at their ends to form, in effect, a hollow tuning fork assembly analogous of two tuning forks joined together at the extremities of their tines. Inlets and outlets are provided at the respective ends of the tubes for a liquid whose density is to be measured and the tubes are vibrated in anti-phase in their natural half wavelength transverse mode. When the tubes are full of a liquid the frequency of the vibrations is dependent upon the density of that liquid and means is provided for measuring this frequency. Such apparatus is capable of measuring the density of a liquid flowing through it to an accuracy of about 0.01% and because the two tubes are vibrating in opposition, the vibration at the ends of the tubes is negligible. However, the requirement that the two tubes should be made identical to each other makes the apparatus relatively expensive. In addition, partitioning the liquid flow into two paths through the apparatus gives rise to a risk of blockage in some applications.

It has also been proposed to use a single tube and to vibrate it in its half wavelength transverse mode. However, the resulting vibrations at the ends of the tube reduce the measurement accuracy to an unacceptable level. One attempt to reduce this disadvantage has been proposed in which the tube is excited in only one mode of transverse vibration having a standing wave pattern with at least two antinodes. The vibrations at the ends of the tube can be reduced thereby but a practicable apparatus would require that the tube be firmly secured to end supports of relatively large mass, thus increasing the cost of the apparatus. In addition the increased frequency of vibration, for a given tube length, would result in greater errors in the measurement of the density of a liquid having entrained air or gas.

SUMMARY OF THE INVENTION

According to the invention there is provided apparatus for determining the density of a fluid comprising a resilient tube, two connecting means secured to the tube at axially-spaced positions, two substantially identical cantilever members each having one end secured to a respective one of the connecting means, and means for exciting natural transverse vibrations in the portion of the tube between the connecting means and in the cantilever members in anti-phase to the vibrations in the tube, each cantilever member having a discontinuity such that, in operation, when the tube is full of fluid of predetermined density, the natural transverse frequency of vibration of each cantilever member is substantially the same as that of the tube and the shear force and bending moment at each connecting means due to vibrations of the cantilever members substantially cancel those due to vibrations of the tube. By discontinuity is meant that there is a change in the ratio $m/EI$ along the length of the cantilever, where $m$ is the mass per unit length, E is equal to the Young's Modulus and I is equal to the second moment of area of the material.

Preferably the cantilever members are secured to their respective connecting means in such a way that they are arranged on a common axis with their free ends directed inwardly towards each other in spaced relation to and substantially parallel to the axis of the tube.

The cantilever members may:
1. be formed of the same material as the tube,
2. be formed of a material having substantially the same modulus of elasticity in flexure and having cross-sectional dimensions such that they have substantially the same second moment of area as the tube,
3. be tubular members having the same bore and wall thickness as the tube and preferably formed of the same material.

In a preferred embodiment both the tube and the cantilever members are right-circular cylindrical tubes of the same material and cross-sectional dimensions.

Each discontinuity may comprise a load means or mass secured to its associated cantilever. The load means or mass may be secured anywhere on the cantilever other than at the root although it is most likely to be secured at or near the free end thereof. In the preferred embodiment the load means or mass is an annular collar. The annular collar is firmly attached to the cantilever by brazing, welding, silversoldering or by some other rigid means. The collar may be designed in such a way that it is in two parts, one part being attached to the cantilever and the second part to the first, by screws or bolts for example. It is convenient to use a split collar in order to inspect and clean the joint area when necessary but it is possible by using other welding techniques, such as electron beam, to make a one piece collar. The actual size of the piece part is determined by that which will ensure a balance of the forces on the root structure joining cantilever and fluid tube when the tube is filled with a fluid of density equal to the centre of the lowest span of the instrument so that other centres may be accommodated by adding to this end mass.

DESCRIPTION OF THE DRAWINGS

The invention will now be described, solely by way of example, with reference to the accompanying drawings, in which.

DETAILED DESCRIPTION OF THE INVENTION

Figure 1:
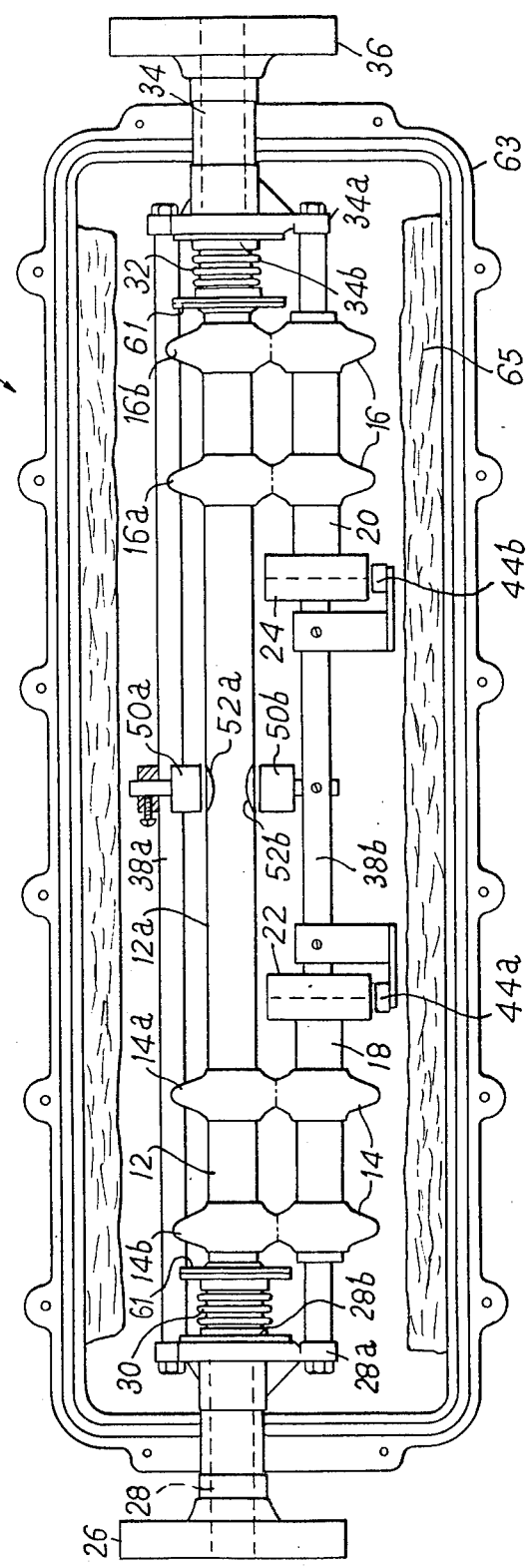
FIG. 1 shows one embodiment of apparatus for determining the density of a liquid.
Figure 2A:
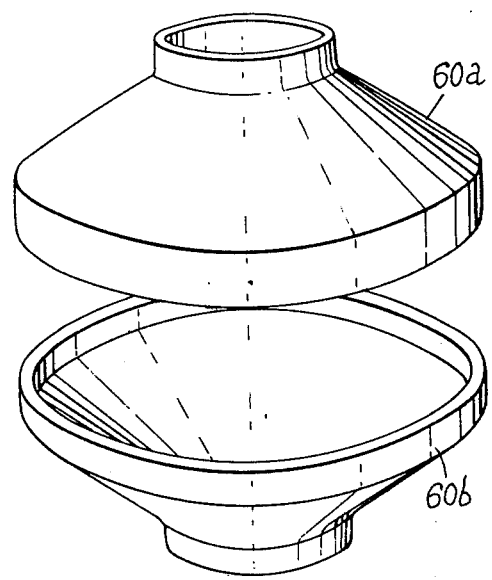
FIG. 2a and b shows exploded perspective and cross-sectional views respectively of part of the connecting means of FIG. 1 to a different scale.
Figure 2B:
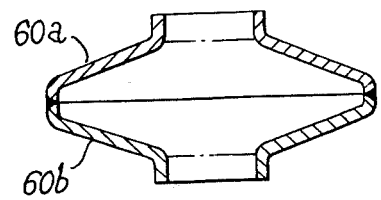

Referring to FIG. 1 the apparatus 10 comprises a tube 12 having an outside diameter of 1 inch and a wall thickness of 0.036 inches. The tube 12 is formed of a resilient material, in this case cold drawn seamless stainless steel tube, although it is envisaged that other materials could be used, such as described hereinafter. Two connecting means 14 and 16 respectively are secured to the tube 12 at axially spaced positions to define a central portion 12a of the tube. Each connecting means is made-up from hollow, double-ended frusto-conical members 60 as hereinafter described with reference to FIGS. 2 and 3. The frusto-conical members 60 of each connecting means are spaced axially along the tube at intervals of about 65 mm between centres and welded to it to form a sub-assembly. The length $L_T$ of the portion 12a of the tube between the centres of the inner two of each pair of cones forming parts 14a and 16a of connecting means 14, 16 is 298 mm and this length determines the natural transverse frequency of vibration of the portion 12a. This frequency will of course, also depend upon the density of the liquid with which the tube 12 is to be filled in operation.

Figure 3:
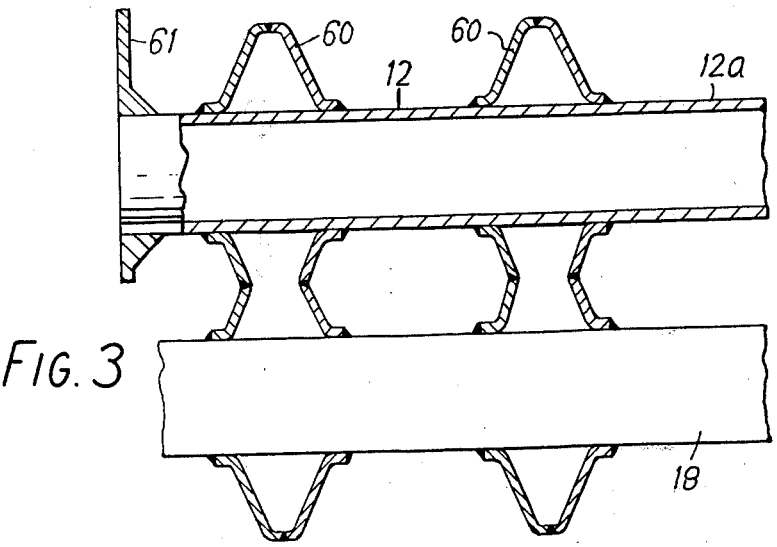
FIG. 3 shows a cross-sectional view of a connecting means of FIG. 1 to a different scale.

Two substantially identical cantilever members 18 and 20 in the form of stainless steel tubes having the same cross-sectional dimensions, and therefore the same second moment of area, as the tube 12 have one end secured to a respective connecting means 14 and 16 as hereinafter described. The frusto-conical members 16 are spaced axially along each cantilever 18, 20 at intervals of about 65 mm between centres and welded to it to form further sub-assemblies. Then each sub-assembly is machined and joined at a common interface, as best seen in FIG. 3. This connecting means is used, to obtain a high natural stiffness, low weight, and simplicity and economy of manufacture using conventional techniques. The frusto-conical members 60a and 60b are made from annular discs blanked from sheet material, then pressed into frusto-conical form and beam welded together. The sub-assemblies 60 are then positioned on the tube 12 and cantilever respectively and the inner edges welded to the tube and the cantilever. A part of each cone 60 is now machined away and the resulting interface matched to a similar assembly on the cantilever and the two parts joined together using argon arc welding. In addition to the cones, flanges 61 are welded on the ends of the fluid tube for subsequent sealing to flexible couplers 30, 32 which isolate the vibrating system from the main instrument frame. The frame comprises three pillers in the form of hexagonal mild steel bars, of which two pillars 38a, 38b are shown and two fittings 28, 34 having lugs 28a, 34a to which the pillars are bolted, a sealing surface 28b, 34b for the flexible couplers 30, 32 and a tubular portion interconnecting the flexible couplers with flanges 26, 36 welded to the end of the tubular section thus making it possible to change the flange type to suit customers requirements. The cantilevers 18 and 20 are arranged on a common axis with their free ends directed inwardly towards each other and, as shown, are in spaced-relation to and substantially parallel to the axis of the tube 12 so that they can vibrate transversely in anti-phase to the tube 12. The length $Lc$ of each cantilever 18, 20 between the centre of the cone 14a, 16a of its respective connecting means and its free end is made such that it has a predetermined natural transverse frequency of vibration equal to that of the tube 12 when the tube 12 is full of a liquid having a predetermined density representative of a density intermediate between the extremes of a range of densities to be measured by the apparatus 10, and preferably at the midpoint of that range. In the example the length $Lc$ of each cantilever is 47.3 mm which gives them a natural transverse frequency of vibration of 990 Hz. The tube 12 has the same natural frequency of 990 Hz when full of liquid having a density of 1000 Kg/cubic metre. Liquid is supplied to the tube by way of an inlet flange 26, a tubular inlet 28 which acts as part of the instrument frame, and a resilient coupling 30 and is discharged by way of a resilient coupling 32 an outlet tube 34 and outlet flange 36. Three bars of which two 38a and 38b are shown, the third being hidden by bar 38a form, together with tubes 28 and 34 the instrument frame. The couplings 30, 32 are stainless steel bellows but may be of various configurations and materials, such as synthetic rubber sleeves, depending upon the application.

Electromagnetic means is provided for exciting the tube 12 and cantilevers 18 and 20 to vibrate continuously at their natural frequency in the transverse mode.

Figure 5:
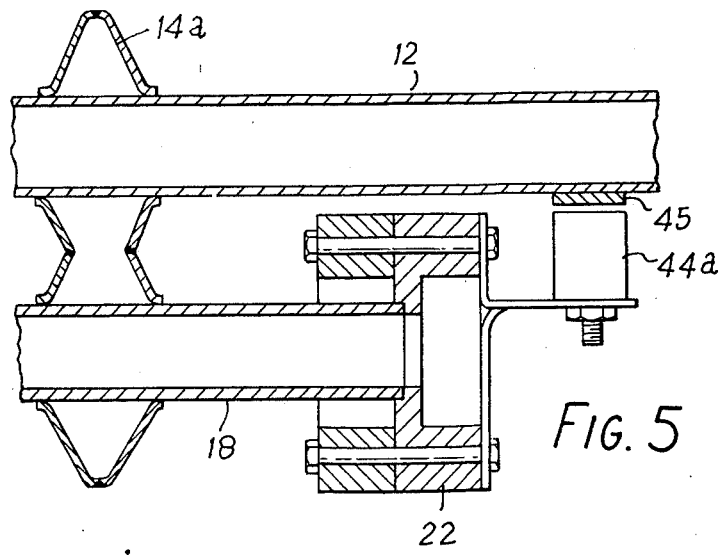
FIG. 5 shows part of another embodiment of apparatus according to the invention in which the pick-up coils are mounted in the cantilever members.

The electromagnetic means comprises a pair of drive coils 50a and 50b for the tube 12, together with small discs 52a and 52b of ferromagnetic material welded to the tube and pick-up coils 44a and 44b for the cantilevers 18 and 20. The coils are arranged with their axes normal to the axis of their respective tube and are positioned as shown. The pick-up coils and drive coils are coupled in known manner to the input and output respectively of a maintaining amplifier (not shown). Each coil is also provided with a bias magnet to prevent frequency doubling. In operation, the tube 12 and cantilevers 18, 20 are set in transverse vibration by either natural mechanical vibration in the system or electrical noise in the circuit and maintained in vibration at their natural frequency by the sustaining loop comprising the drive and pick-up coils and the amplifier. When the tube 12 is caused to vibrate, the resulting movement at its roots is reflected through the connecting means 14, 16 to the cantilevers 18, 20 which react by moving in antiphase to tend to cancel movement caused by the tube. The pillars 38 act as support members for the excitation coil assembly 50a, 50b and the vibration detection coil assembly 44a, 44b. Alternatively the vibration detection coil may be mounted directly onto the tube assembly if excessive lateral movements of the tube assembly on the flexible couplers 30, 32 is likely which would in turn introduce large changes in the small air gaps between the tubes and the detector. FIG. 5 shows one way of mounting the vibration detection coils on the cantilever members with a small magnetic disc 45 secured to the tube 12.

The frame and tube assembly is housed in a cast aluminium waterproof box 63 with the frame end extensions 28, 34 and flanges 26, 36 external. The box 63 is lined with a sound absorbent material 65. The associated electronics are housed separately in a box which may be attached to the main housing or mounted remotely.

The frequency of the vibrations is dependent upon the density of the fluid with which the tube is filled and a frequency meter (not shown) is provided for measuring the frequency of vibrations of the tube and displaying the measured value in units of density.

The cantilevers 18 and 20 are provided with discontinuities in the form of annular collars 22 and 24 secured to the free ends of the cantilevers 18 and 20 respectively. Each collar is of a similar material to that of the cantilevers and has an outside diameter of 56 mm, a wall thickness of 14mm and a length of 12 mm and is so positioned that it is symmetrical about the end plane normal to the axis of its associated cantilever.

Figure 4:
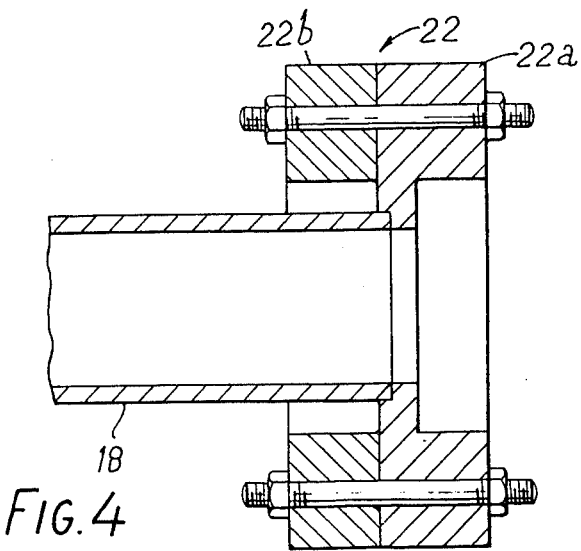
FIG. 4 shows a cross-sectional view of part of a cantilever member of FIG. 1 provided with a discontinuity.

FIG. 4 shows a cross-sectional view of part of a cantilever with its collar. The collar comprises a first part 22a in the form of a flange welded to the end of the cantilever 18 and a second, annular part 22b bolted to the part 22a. It will be seen that the inside diameter of the part 22b is greater than the external diameter of the cantilever 18 so that there is no physical contact between the two. For higher density ranges further annular members would be bolted on to the part 22a symmetrically about the end plane of the cantilever.

The cantilevers 18, 20 with their collars 22 and 24 are so arranged that when the tube 12 and cantilevers are vibrated at their predetermined natural frequency of 990 Hz, that is the tube 12 is full of a liquid of density 1000 Kg/cubic metre, the shear force and bending moment at the roots of the tube, the position at which the ends of the tube meet the connecting means, due to the vibrations in the tube are cancelled by the shear force and bending moments at the roots of the cantilevers due to the vibrations in the cantilevers. Thus the connecting means 14, 16 may be of relatively small mass.

The root shear forces and bending moments, are of course, cancelled only at one predetermined resonant frequency which occurs when the tube is full of liquid of the predetermined density. As the density of the liquid departs from this predetermined value, the root shear forces and bending moments at the connecting means will not cancel with the result that increasing vibration arises at the ends of the tube 12. The frequency of vibration thus becomes increasingly influenced by the mechanical impedances of external structures coupled to the apparatus with a resulting deterioration in accuracy of measurement. By the use of flexible couplers 30, 32 the effect of such mechanical impedances is reduced. Thus the apparatus will have a measurement accuracy which is a maximum at a centre density but which deteriorates as density departs in either direction from the centre density. However, liquid density differs from many other physical variables in that most industrial applications require only a narrow dynamic range of measurements. Almost all applications fall within a 4:1 range of density, that is between about 500 to 2000 kilogrames per metre cube. It is believed that apparatus can be produced having acceptable measurement accuracies over a reasonable density span. For example, it is believed that for a 10% span of density apparatus according to the invention could be rated at full accuracy of 0.05% of the actual density being measured, and for a 30% span at an accuracy which suffers a 4:1 reduction at the extremes of the span. However, the disadvantage arising from the acceptance of a narrow density span is to some extent compensated in that other problems, such as those associated with linearisation, the frequency not being directly proportional to liquid density, are simplified.

It was found that apparatus as described above and made from cold drawn seamless stainless steel having a Young's modulus of elasticity, E, of $29.2 \times 10^6$ lb/sq. in. had a resonant frequency of transverse vibration with air in the tube 12 of 1315 Hz and with water (density 1000 Kg/cubic metre) of 990 Hz.

The stainless steel used for the tube and cantilevers was made according to American Iron and Steel Institute grade A1S1 321 with the following typical composition:

| | |
|---|---|
| Chromium | 17/20 % |
| Nickel | 9/13 % |
| Carbon | .08 % |
| Silicon | .75 % |
| Manganese | 2.0 % max |
| Titanium | 5 × Carbon min. | and is approximately the same as B.S.970 Pt 4 321S12 and the following typical mechanical properties:

| | |
|---|---|
| Ultimate tensile strength | = 85,000 p.s.i. |
| Yield | = 35,000 p.s.i. | in its as drawn tube form.

In a practical embodiment Ni-Span-C Alloy 902 (trade mark) or a ferromagnetic stainless steel could be substituted for austenitic stainless steel.

Ni-Span C 902 is made by: Huntington Alloy Products Division, The International Nickel Company, Inc. Huntington 17, West Virginia, and in Bulletin T31 entitled "Engineering properties of Ni-Span-C iron nickel-chromium alloy 902" it is stated to have the following constituents:

| | |
|---|---|
| Nickel (plus cobalt) | 41.0 to 43.50 |
| Chromium | 4.90 " 5.75 |
| Titanium | 2.20 " 2.75 |
| Aluminium | 0.30 " 0.80 |
| Carbon | 0.06 max. |
| Manganese | 0.80 " |
| Silicon | 1.00 " |
| Sulphur | 0.04 " |
| Phosphorus | 0.04 |
| Iron | remainder, and |

Young's Modulus $E = 24 \times 10^6$ to $29 \times 10^6$ lbs/sq. in. Density = 0.293 lb/cubic inch. Ni-Span-C Alloy 902 finds useful application because it has a very low temperature co-efficients of Young's modulus, dependent to some extent upon the degree of cold working it is subjected to and its subsequent heat treatment.

A typical ferromagnetic stainless steel which can be used for the tube and cantilevers is that known under the type number FV520(S) and described in a publication entitled "Mechanical and Physical Properties of Staybrite and Stainless Steels" published by Firth Vickers Stainless Steels Limited as having a composition:

| | |
|---|---|
| Carbon | 04/.07 |
| Silicone | 0.6 max. |
| Manganese | 1.0 max. |
| Chromium | 13.2/14.7 |
| Nickel | 5.0/6.0 |
| Copper | 1.2/2.0 |
| Molybdenum | 1.2/2.0 |
| Niobium | 0.2/0.7 | and modulus of Elasticity $29.2 \times 10^6$ lb/sq. in.

As described above the shear force and bending moment at the roots of the tube are cancelled by those due to the cantilevers at one frequency of vibration only, representative of a given density of liquid in the tube. This density (and frequency) may be regarded as the centre density (and centre frequency) of a range of densities to be measured by the apparatus.

If the desired centre density is changed then some of the dimensions of the apparatus must be changed accordingly.

One method of calculating the dimensions of parts of the apparatus for a liquid centre density $\rho_R$ is as follows:

Nomenclature

| | |
|---|---|
| B | bore diameter of tube |
| D | outer diameter of tube |
| b | tube wall thickness = ½ (D-B) |
| E | modulus of elasticity in flexure |
| $\rho_M$ | weight/unit volume of tube material |
| $\rho_L$ | weight/unit volume of liquid |
| $\rho_N$ | value of $\rho_L$ at density span centre |
| m | mass/unit length |
| I | moment of inertia (second moment) of section area |
| L | length of vibrating component |
| x | length variable |
| y | vibration displacement normal to x | suffix T and suffix C will be used for the tube and cantilever respectively, where required to avoid ambiguity.

The length $L_T$ of the tube 12 is first determined. The length is not critical but may simply represent a compromise between the conflicting desires for low frequency (i.e. longer tube) and the installation appeal of a short length transducer.

Consider a tube (fluid filled) to be resonant in the half wavelength mode with end constraints such that, at the extremities, values of both $y$ and $dy/dx$ are zero at all times. In beam deflection terminology, this is the case of the "built in beam".

At span centre density, the required natural frequency is given by:

$$f_T = \frac{0.8925}{L_T^2} \sqrt{\frac{E(D^2 + B^2)(D^2 - B^2) \cdot g}{(D^2 - B^2)\rho m + B^2 \rho r}}$$

The bore B will be determined to some extent by the application, and the wall thickness of the tube may be of such a value that the mass of the tube is approximately equal to that of the liquid of density $\rho$ with which the tube is to be filled in use.

For a tube and cantilever with static built-in roots the following equations apply:

| | CANTILEVER | TUBE |
|---|---|---|
| Frequency | $w_c^2 = \frac{E_c I_c \cdot (1.87510)^4}{m_c L_c^4}$ | $w_T^2 = \frac{E_t I_t \cdot (4.73004)^4}{m_t L_T^4}$ |
| Root Shear Force | $\frac{w_c^2 m_c y_c}{K_c} \cdot \cot\tfrac{1}{2}K_c L_c$ | $\frac{w_t^2 m_t y_t}{K_t} \cdot \frac{2\sinh\tfrac{1}{2}K_t L_t \cdot \sin\tfrac{1}{2}K_t L_t}{(\sinh\tfrac{1}{2}K_t L_t + \sin\tfrac{1}{2}K_t L_t)}$ |
| Root Bending Moment | $\frac{w_c^2 m_c y_c}{K_c^2}$ | $\frac{w_t^2 m_t y_t}{K_T^2} \cdot \frac{2\sinh\tfrac{1}{2}K_t L_t \cdot \cos\tfrac{1}{2}K_t L_t}{(\sinh\tfrac{1}{2}K_t L_t + \sin\tfrac{1}{2}K_t L_t)}$ | where $K^4 = mw^2/EI$ and $w = 2\pi \times$ frequency.

For a tube freely hinged at its roots, that is with zero root stiffness, the equation for frequency of vibration is;

$$W^2 = \frac{E_T I_T (3.142)^4}{m_T L_T^4}$$

It has been found that by securing the tube and cantilevers in accordance with the present invention, the numerical constant in the above two equations for the frequency of vibration of the tube is within an approximate mid-range between the constants for a tube with static built-in roots and one freely hinged at its roots.

At the centre density $\rho$, the frequencies of the tube and cantilever must be equal and the rroot shear forces and bending moments of the cantilevers must cancel those of the tube for the condition of no end movement. The dimensions of the cantilever for such condition can be obtained from the above equations.

Although a discontinuity in the form of an annular collar 22 or 24 has been described, other discontinuities in the form of one or more masses, or one or more changes in dimension, such that there is a change in the ratio m/EI along the length of the cantilever are envisaged.

While the invention has been described in relation to the measurement of the density of a liquid, the apparatus could, by modification of its dimensions, be used to measure the density of a gas.

I claim;

1. Apparatus for determining the density of a fluid comprising a resilient tube, two connecting means secured to the tube at axially-spaced positions along the tube, two substantially identical cantilever members each having one end secured to a respective one of the connecting means and a free end, and means for exciting natural transverse vibrations in the portion of the tube between the connecting means and in the cantilever members in anti-phase to the vibrations in the tube, each cantilever member having a discontinuity such that when the tube is full of fluid of predetermined density, the natural transverse frequency of vibration of each cantilever member is substantially the same as that of the tube and the shear force and bending moment at each connecting means due to vibrations of the cantilever members substantially cancel those due to vibrations of the tube.

2. Apparatus according to claim 1, in which the cantilever members are secured to their respective connecting means in such a way that they are on a common axis with their free ends directed inwardly towards each other in spaced relation to and substantially parallel to the axis of the tube.

3. Apparatus according to claim 2, in which the cantilever members are of the same material as the tube.

4. Apparatus according to claim 2, in which the cantilever members are formed of a material having substantially the same modulus of elasticity in flexure and have cross-sectional dimensions such that they have substantially the same second moment of area as the tube.

5. Apparatus according to claim 4, in which the cantilever members are of the same material as the tube and are tubular members having the same bore and wall thickness as the tube.

6. Apparatus according to claim 2, in which the cantilever members are tubular members having the same bore and wall thickness as the tube.

7. Apparatus according to claim 2, in which the tube and the cantilever members are right-circular cylindrical tubes of the same material and cross-sectional dimensions.

8. Apparatus according to claim, 7 in which each discontinuity comprises a load means or mass on its associated cantilever.

9. Apparatus according to claim 8, in which the load means or mass is secured at or near the free end of its associated cantilever.

10. Apparatus according to claim 9, in which the load means or mass comprises an annular collar.

11. Apparatus according to claim 10, in which the annular collar comprises a first part secured to the cantilever and a second part, and means for removably securing the second part to the first part.

12. Apparatus according to claim 9, comprising two support means, two resilient coupling members coupled between respective ends of the tube and the support means, whereby the tube is resiliently mounted on said support means.

13. Apparatus according to claim 12, in which the means for exciting natural vibrations in the tube comprises at least one drive coil and at least one vibration-detection coil, means for so mounting the coils that their axes are normal to the tube and means for coupling the coils to the output and input terminals respectively of a maintaining amplifier such that, in operation, the tube and cantilevers are maintained in vibration at their natural frequency.

14. Apparatus according to claim 13, in which there are two drive coils having a common axis and disposed on diametrically opposed sides of the tube.

15. Apparatus according to claim 13, in which the vibration detection coil is positioned and arranged to detect the vibrations in a respective cantilever member.

16. Apparatus according to claim 15, in which the tube and cantilever members are of non-ferromagnetic material and pieces of ferromagnetic material are secured to the tube and cantilever to provide a flux path from a drive coil to the tube and from a vibration detection coil to a cantilever member as the case may be.

17. Apparatus according to claim 13, in which the drive and vibration detection coils are mounted on the support means.

18. Apparatus according to claim 13, in which the drive coil is mounted on the support means and the vibration detection coil is mounted on a cantilever member.

19. Apparatus according to claim 13, in which the cantilever members have the same bore and wall thickness as the tube.

20. Apparatus according to claim 1, in which each discontinuity comprises a load means or mass on its associated cantilever.

21. Apparatus according to claim 20, in which each load means or mass is at or near the free end of its associated cantilever.

22. Apparatus for determining the density of a fluid comprising a resilient tube, two connecting means secured to the tube at axially-spaced positions along the tube, two substantially identical cantilever members each having a free end and a fixed end so secured to a respective one of the connecting means that they are on a common axis with their free ends directed inwardly towards each other in spaced relation to and substantially parallel to the axis of the tube, two support members for the tube, two resilient coupling members coupled between respective ends of the tube and the support members, and means for exciting natural transverse vibrations in the portion of the tube between the connecting means and in the cantilever members in anti-phase to the vibrations in the tube, each cantilever member having a discontinuity such that when the tube is full of fluid of predetermined density, the nautral transverse frequency of vibration of each cantilever member is substantially the same as that of the tube and the shear force and bending moment at each connecting means due to vibrations of the tube.

23. Apparatus according to claim 22, in which the cantilever members are tubular members of the same material as and having the same bore and wall thickness as the tube.

24. Apparatus according to claim 22, in which the tube and the cantilever members are right-circular cylindrical tubes of the same material and cross-sectional dimensions.

25. Apparatus according to claim 24, in which each discontinuity comprises a load means or mass secured at or near the free end of its associated cantilever.

26. Apparatus according to claim 25, in which the load means or or mass comprises an annular collar.

27. Apparatus according to claim 25, in which the means for exciting natural vibrations in the tube comprises at least one drive coil and at least one vibration-detection coil, means for so mounting the coils that their axes are normal to the tube and means for coupling the coils to the output and input terminals respectively of a maintaining amplifier such that, in operation, the tube and cantilevers are maintained in vibration at their natural frequency.

28. Apparatus for determining the density of a fluid comprising a resilient tube, means for admitting the fluid into said tube, two connecting means secured to said tube at axially-spaced positions along said tube, two substantially identical cantilever members each secured to a respective one of said connecting means, and means for exciting natural transverse vibrations in the portion of said tube between the connecting means and in said cantilever members in anti-phase to the vibrations in said tube, each of said cantilever members having means arranged thereon and cooperating therewith for substantially nulling the vibrations at said connecting means when said tube is full of a fluid of predetermined density.

29. Apparatus according to claim 28, further including means for providing a representation of the density of the fluid as a function of frequency of vibration of said tube.

* * * * *

UNITED STATES PATENT OFFICE
CERTIFICATE OF CORRECTION

Patent No. 3,955,401           Dated August 12, 1976

Inventor(s) Reginald Catherall

It is certified that error appears in the above-identified patent and that said Letters Patent are hereby corrected as shown below:

On the title page omit the Assignee "Bell & Howell Company, Chicago, Illinois", and add the Assignee --Bell & Howell Limited, Lennox Road, Basingstoke, Hampshire, England--.

Column 5, line 46, "Howeveer" should be --However--.
Column 7, line 45, after "p" add --r--.
Column 8, line 8, "p" should be --pr--.
Column 8, line 9, "rrot" should be --root--.
Column 10, line 18, after "vibrations" insert --of the cantelever members substantially cancel those due to vibrations--.
Column 10, line 32, delete the second occurrence of "or".
Column 10, line 43, after "comprising" insert --:--.

Signed and Sealed this

Twenty-eighth Day of September 1976

[SEAL]

Attest:

RUTH C. MASON
Attesting Officer

C. MARSHALL DANN
Commissioner of Patents and Trademarks